United States Patent [19]
Kocur et al.

[11] Patent Number: 5,338,297
[45] Date of Patent: Aug. 16, 1994

[54] CERVICAL CANAL BALLOON CATHETER

[75] Inventors: Walter Kocur, Yonkers; Basil Kocur, Buffalo, both of N.Y.

[73] Assignee: Kocur Medical Associates, Yonkers, N.Y.

[21] Appl. No.: 34,675

[22] Filed: Mar. 19, 1993

[51] Int. Cl.⁵ .............................................. A61M 29/00
[52] U.S. Cl. ........................................ 604/96; 606/193
[58] Field of Search ............... 604/96, 101, 103, 108, 604/117, 174, 178; 606/192, 193, 196

[56] References Cited

U.S. PATENT DOCUMENTS

| | | | |
|---|---|---|---|
| 669,910 | 3/1901 | Ball | 604/103 |
| 2,457,244 | 12/1948 | Lamson | 604/96 |
| 2,936,760 | 5/1960 | Gants | |
| 3,253,594 | 5/1966 | Matthews et al. | 604/96 |
| 3,587,588 | 6/1971 | Murr | 606/193 |
| 4,100,923 | 7/1978 | Southern | |
| 4,177,815 | 12/1979 | Patel | 604/103 |
| 4,430,076 | 2/1984 | Harris | |
| 4,496,345 | 1/1985 | Hasson | 604/103 |
| 4,693,704 | 9/1987 | Ogita | |

FOREIGN PATENT DOCUMENTS 2612783  9/1988  France ........................... 606/193

*Primary Examiner*—John D. Yasko
*Assistant Examiner*—Anthony Gutowski
*Attorney, Agent, or Firm*—Herbert Dubno

[57] ABSTRACT

A cervical canal obturator and infusing catheter comprises a threaded metal tube formed at one end with a balloon adapted to be expanded and snugly fit against the internal cervical os while a ring threaded onto the tube bears against the external cervical canal and is locked against unscrewing by a locking nut also on the outer tube. An inner tube within the outer tube can deliver an infusing or antibiotic solution into the uterus or withdraw amniotic fluid and can be held in the outer tube between a pair of plugs said into the outer tube.

5 Claims, 3 Drawing Sheets

CERVICAL CANAL BALLOON CATHETER

FIELD OF THE INVENTION

Our present invention relates to a cervical canal obturator and catheter and, more particularly, to a device adapted to be inserted into the cervical canal and to block uncontrolled escape of fluid therefrom and permit irrigation of the uterus or womb through the cervix.

BACKGROUND OF THE INVENTION

In U.S. Pat. No. 4,693,704, a cervical canal catheter is described which is intended to treat premature rupture of the membrane before the beginning of parturition, efflux of amniotic fluid from the womb and the onset of parturition.

In that arrangement, a two lobe balloon seal is inserted into the cervical canal and the balloons are inflated or expanded so that one of the balloons seats primarily at the isthmus of the uterus while the other is located generally within the canal. Key to this system, in addition to the gourd-shape of the balloon which engages at the isthmus of the uterus, is the provision of or a requirement for a ligature which extends through the body of the cervix between these tubes to prevent the widening of the cervical canal and ejection of the stopper formed by this assembly.

The goal is to prevent amniotic fluid from efflux through the cervical canal.

The device also provides a tube which extends through the balloon and provides communication with the uterus or womb so that amniotic fluid can be withdrawn in premature rupture of the membranes.

In practice, the requirement for the ligature in the wall of the cervix in the region of the inserted plug between the two balloons has been found to be disadvantageous because the application of the ligature is an invasive procedure and may be a cause of preterm labor.

Without the ligature, the stopper may be ineffective.

Mention may also be made of U.S. Pat. No. 4,100,923 which provides a balloon which fits into the cervix and has a pair of resilient flanges, one of which forms a cup over the mouth of the cervix while the other lies across the cervical canal within the womb.

The balloon is inflated through one passage and a further passage extends through the balloon to administer medication to the extra amniotic space in an impregnated uterus, e.g. for abortion.

This arrangement also has been found to be disadvantageous as a plug for the cervix and depends, for its sealing effectiveness, upon the balloon practically completely filling the cervical canal and the distortion of the cervical canal upon introduction to allow the relatively large flange which seats against the inner end of the canal, to provide the seal.

Mention may also be made of U.S. Pat. No. 4,430,076 which provides a uterine manipulative and injection device which engages in the womb and expands against the isthmus of the cervical canal and operates with a fixedly positioned enlargement or stop surface. This device is complex to insert and also has not been found to be fully satisfactory.

Finally, reference may be had to the pressure positive catheter described in U.S. Pat. No. 2,936,760 which is intended for insertion into the urethra and to be able to close both ends of the urethra in conjunction with introduction of a medium into the urethra of a female patient, particularly in connection with positive pressure urethrography. In that system, as well, two expandable balloon elements are provided.

Objects of the Invention

It is therefore an object of the present invention to provide an improved cervical obturator or stopper, which can be used for instillation of antibiotic solution into the womb or uterus and which can be set in place more effectively than earlier devices.

Another object is the provision of such an improved cervical obturator or stopper, can be used for irrigation of the womb or uterus and which can be set in place more effectively than earlier devices which overcomes the above-given disadvantages, that is which is of comparatively low cost but can be positioned and removed with ease and with a minimum of strain upon the patient.

Still another object of this invention is to provide a cervical plug and catheter which can be used without the need for a cervical canal ligature.

SUMMARY OF THE INVENTION

These objects and others which will become apparent hereinafter are attained, in accordance with the present invention in a cervical obturator and catheter which comprises a tube, preferably of stainless steel, having a leading end formed with a neck between a pair of bosses on each of which a respective hole in an expandable silicone or equivalent elastomer balloon is engaged, the tube communicating with this balloon and having a connection to a catheter check valve at the opposite end of the tube through which a flowable medium can be injected past a check valve to expand the balloon or from which the expansion medium can be withdrawn to allow the balloon to deflate or contract. According to the invention, moreover, another tube extends through the first to communicate with the interior of the womb or uterus at the inner end of the outer tube, while the outer end of the inner tube is fitted with a female luer connection for attachment to a syringe by means of which fluid can be withdrawn from the womb or uterus, or a solution can be infused into the womb.

In accordance with an important aspect of the invention, at least a limited portion of the length of the outer tube is formed with an eternal screwthread on which an internally threaded ring and a locking nut are carried, which, like the outer tube, can preferably be composed of stainless steel or other sterilizable material.

According to the invention, therefore, the plug is engaged in the internal cervical os while the ring is threaded along the outer tube until the snugly engages the external cervical os and is there locked in place by the locking nut.

With this device where the outer member retaining the stopper in place is a combination of an internally threaded ring and an internally threaded locking nut. The physician can easily position the device and hold it in place without the need for a circumferential ligature in the cervical canal wall.

According to a feature of the invention, the inner tube is anchored in the outer tube in a pair of plugs of plastic material, e.g. a polysulfone, force fitted into the outer tube so that the passage communicates with the balloon defined between the inner tube and these two plugs with the outer tube.

BRIEF DESCRIPTION OF THE DRAWING

The above and other objects, features, and advantages will become more readily apparent from the following description, it being understood that any feature described with reference to one embodiment of the invention can be used where possible with any other embodiment and that reference numerals or letters not specifically mentioned with reference to one figure but identical to those of another refer to structure that is functionally if not structurally identical. In the accompanying drawing.

Specific Description

Figure 4:
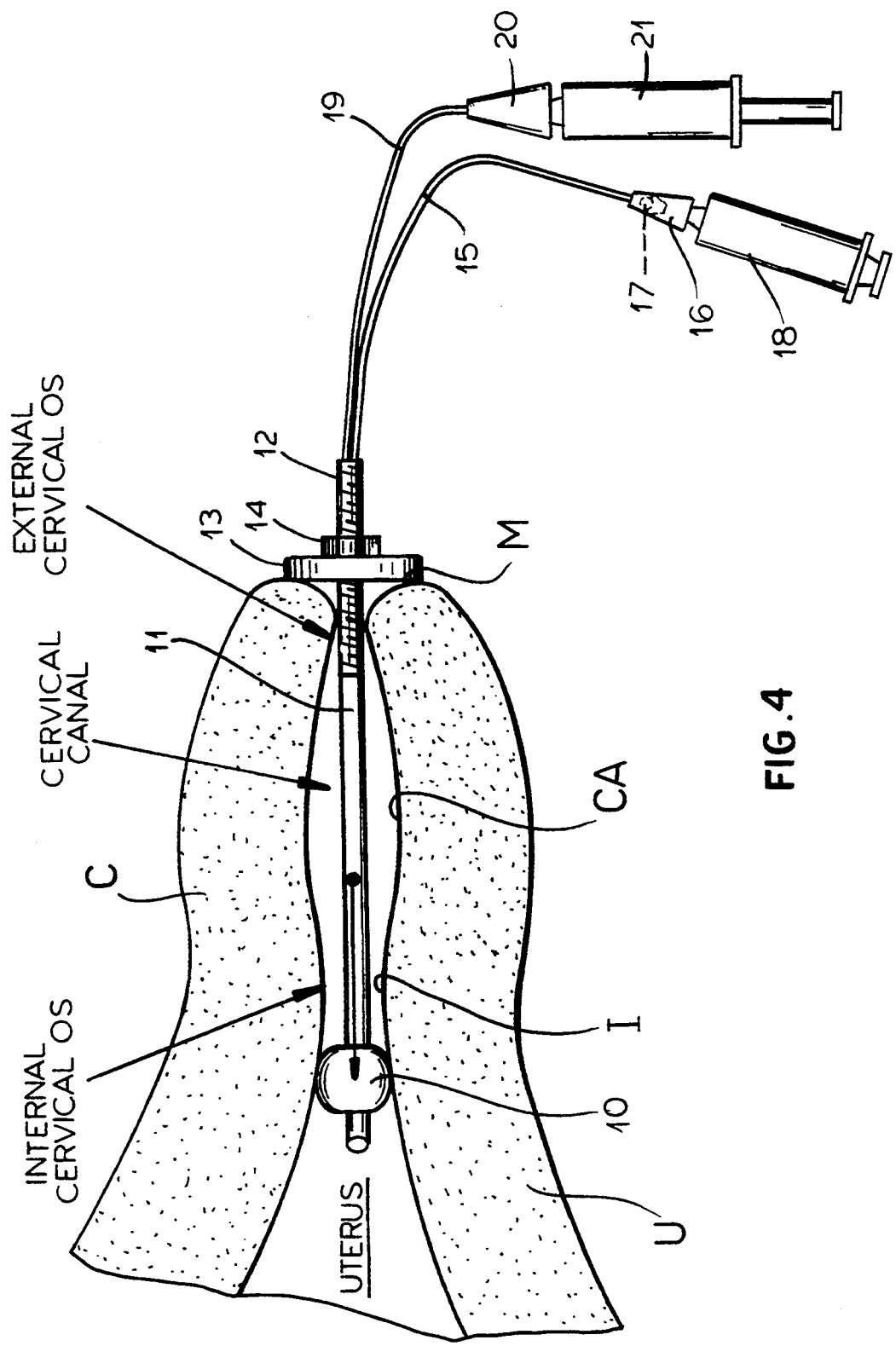
FIG. 4 is a diagrammatic section through the cervix of a uterus showing the device in place.

As seen in FIG. 4, the stopper of the present invention is intended to be inserted into the cervical canal CA of a cervix C of a uterus U. The stopper comprises a balloon 10 which can be expanded against the internal cervical os, an outer tube 11 formed with an external screw thread 12 and a ring 13 having an internal screw thread mating with the external screw thread and bearing upon the external cervical os.

A lock nut 14 secures the ring 13 in place.

Medical tubing 15 is connected to the passage in the tube 11 communicating with the balloon 10 and has a catheter check valve represented diagrammatically by the ball 17, and receives a syringe 18 for inflating the balloon. When the syringe is inserted, the ball can be displaced to allow expansion or contraction of the balloon. When the syringe 18 is removed, the ball check valve 17 can maintain the balloon 10 in its inflated condition.

Medical tubing 19 serves to irrigate the uterus and also has a female luer connector 20 which can be connected to a syringe 21 containing the solution to be introduced into the uterus.

Figure 1:
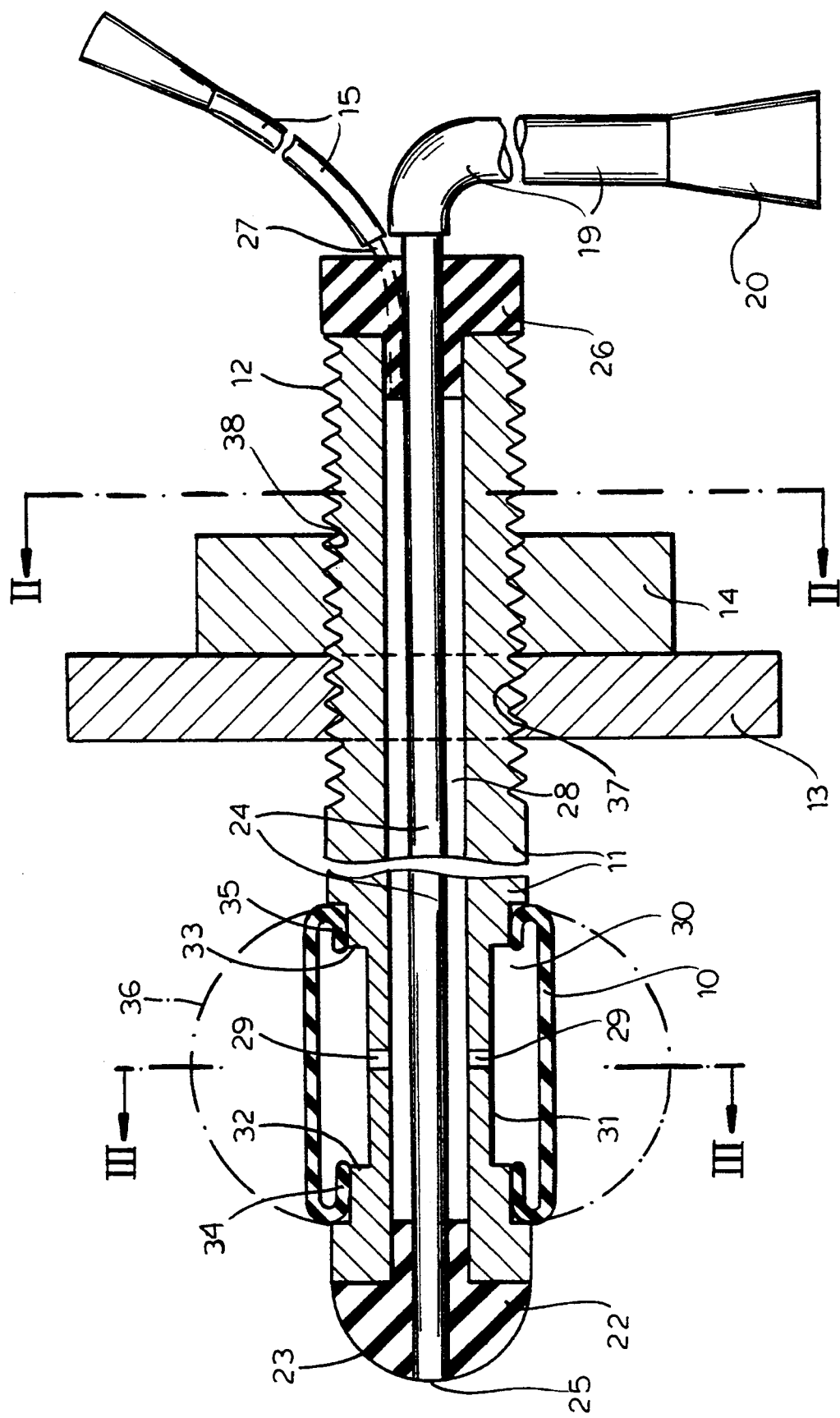
FIG. 1 is an axial cross sectional view of the cervical stopper or catheter assembly, according to the invention, with portions being shown of exaggerated size for clearer illustration.
Figure 3:
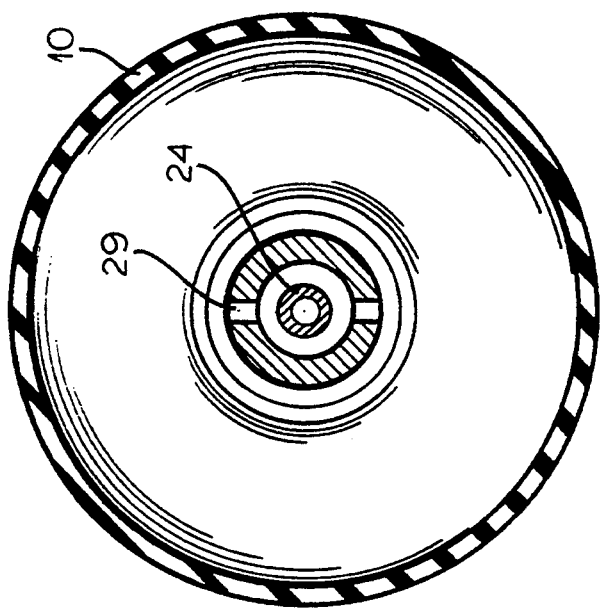
FIG. 3 is a cross sectional view taken along the line III—III of FIG. 1 but with balloons thereof in an expanded state.
Figure 2:
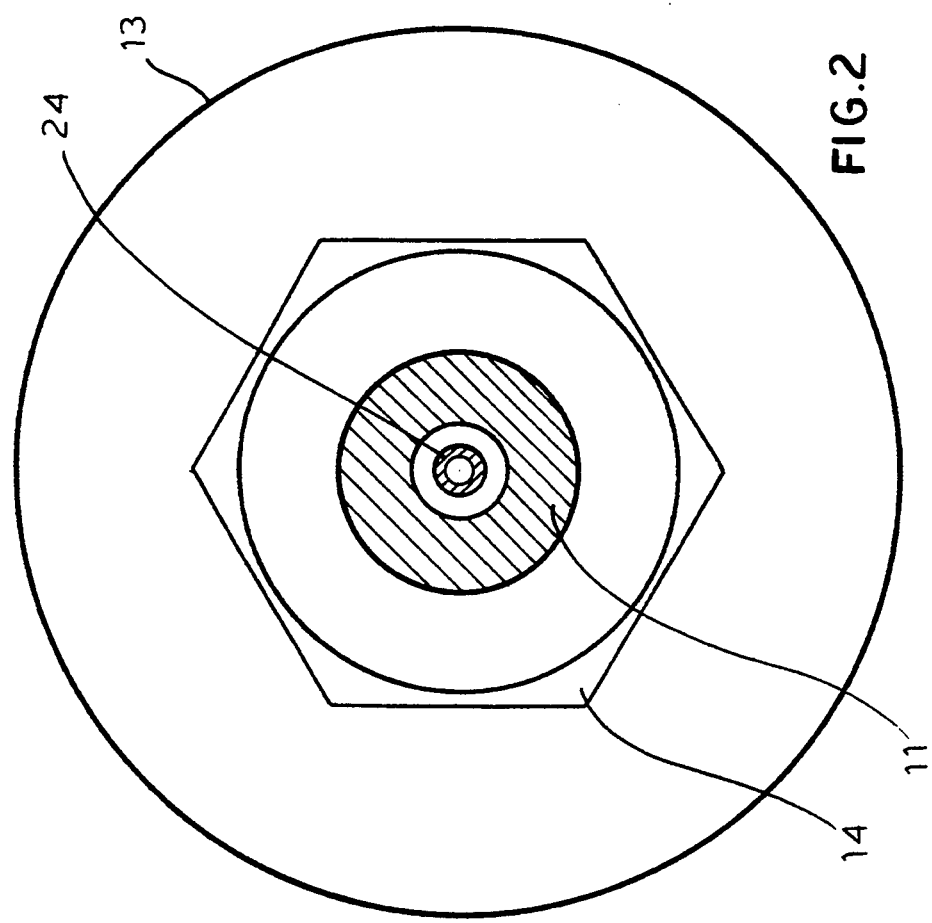
FIG. 2 is a cross sectional view taken along the section line II—II of FIG. 1.

From FIGS. 1 to 3, it will be apparent that the tube 11 is formed at its inner end with a plug 22 of plastic which can be rounded at 23 to facilitate insertion into the cervix. The plug 22 is traversed by and supports an inner tube 24 which can be composed of stainless steel and opens at 25 into the womb or uterus to deliver a solution into the uterus or withdraw fluid therefrom. The stainless steel tube 24 is supported at its opposite end in a plug 26 which is provided with a tube 27 communicating with the medical tubing 15 previously described and opening into a passage 28 between the tube 24 and the outer tube 11.

The passage 28 communicates with radial bores 29, of which two have been shown. The radial bore opens into a chamber 30 defined by a reduced diameter neck 31 of the stainless steel tube 11 located between a pair of bosses 32 and 33 upon which the inner collars of the silicone balloon 10 are sealingly engaged by crimping down the stainless steel tubing around it (see drawing).

As will be apparent from the dot-dash line shown in FIG. 1, when physiological sterile solution is fed to the balloon by the syringe 18, the balloon can be expanded at 36 to engage the interval cervical os.

The ring 13 is shown to be circular and to be of a larger diameter than the nut 14 to be certain that it engages the external cervical canal securely. It has an internal screwthread 37 enabling it to be screwed along the external screw thread 12 of the outer tube 11 to engage the mouth of the cervix. The nut 14 has an internal screwthread 38 enabling it to be locked against the ring 13.

In use, the device is inserted into the cervical canal by the physician and the ring 13 is threaded up against the external cervical os and the balloon inflated to anchor the device in place.

To prevent loosening the nut 14 is tightened against the ring. The desired solution can then be infused into the uterus or a sample of amniotic fluid can be sampled.

When the device is to be removed, the balloon is deflated and, if necessary, the nut 14 and ring 13 are threaded along the tube 12.

We claim:

1. A device for sealing the cervical canal and infusing a solution therein which comprises:

an outer tube having an inner end receivable in a cervical canal and an outer end remote from said inner end, said outer tube being formed with an external screwthread over a region thereof proximal to said outer end;

an expandable balloon mounted on said inner end of said outer tube;

an inner tube extending through said outer tube and adapted to communicate it to said inner end with the uterus;

a ring threaded onto said external screwthread and adapted to be screwed therealong up against the external cervical os;

a locking nut threaded on said outer screwthread and engageable with said ring for locking same against unscrewing;

means at said outer end for expanding said balloon to engage a wall of said internal cervical os;

means at said outer end for infusing a solution into said inner tube for delivery to the uterus, said outer tube being stainless steel tube formed at said inner end with a reduced-diameter portion defining a chamber within said balloon and at least one passage communicating with said chamber, said inner and outer tubes defining a channel for delivering a balloon-expanding fluid to said chamber, said outer tube being formed with a pair of bosses on opposite sides of said reduced-diameter portion and sealingly receiving collars of said balloon, and plugs in said inner and outer ends of said outer tube traversed by said inner tube and supporting same in said outer tube.

2. The device defined in claim 1 wherein said plugs are composed of plastic and said balloon is composed of silicone rubber and said tubes are composed of stainless steel.

3. The device defined in claim 2 wherein said means for expanding said balloon includes a length of medical tubing communicating with said channel and a catheter check valve adapted to receive a syringe and connected to said length of medical tubing.

4. The device defined in claim 3, further comprising another length of medical tubing connected to said inner tube at said outer end and formed with a female luer connector connectable with a syringe.

5. The device defined in claim 4 wherein said plug at said inner end of said outer tube is rounded to facilitate insertion of said device into the cervical canal.

* * * * *